United States Patent
Zhou et al.

(10) Patent No.: US 9,908,851 B2
(45) Date of Patent: Mar. 6, 2018

(54) 2-PIPERIDINYL SUBSTITUTED N,3-DIHYDROXYBUTANAMIDES

(71) Applicant: Duke University, Durham, NC (US)

(72) Inventors: Pei Zhou, Durham, NC (US); Eric J. Toone, Durham, NC (US); Robert A. Nicholas, Chapel Hill, NC (US)

(73) Assignees: Duke University, Durham, NC (US); University of North Carolina Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/912,137

(22) PCT Filed: Aug. 18, 2014

(86) PCT No.: PCT/US2014/051504
§ 371 (c)(1),
(2) Date: Feb. 15, 2016

(87) PCT Pub. No.: WO2015/024016
PCT Pub. Date: Feb. 19, 2015

(65) Prior Publication Data
US 2016/0200682 A1    Jul. 14, 2016

Related U.S. Application Data

(60) Provisional application No. 61/866,857, filed on Aug. 16, 2013.

(51) Int. Cl.
| | |
|---|---|
| A61K 31/445 | (2006.01) |
| C07D 211/08 | (2006.01) |
| C07D 211/06 | (2006.01) |
| C07D 211/14 | (2006.01) |
| A61K 31/455 | (2006.01) |

(52) U.S. Cl.
CPC .......... *C07D 211/06* (2013.01); *C07D 211/14* (2013.01); *A61K 31/455* (2013.01)

(58) Field of Classification Search
CPC ............. C07D 211/14; A61K 31/445
USPC ........................... 514/317; 546/192
See application file for complete search history.

(56) References Cited

U.S. PATENT DOCUMENTS

| | | | |
|---|---|---|---|
| 5,712,300 A | 6/1998 | Jacobsen | |
| 6,495,568 B1 | 12/2002 | Dack et al. | |
| 6,511,993 B1 | 1/2003 | Dack et al. | |
| 7,119,203 B2 | 10/2006 | Barta et al. | |
| 7,358,359 B2 | 4/2008 | Andersen et al. | |
| 7,691,843 B2 | 4/2010 | Raju et al. | |
| 7,989,660 B2 | 8/2011 | Andersen et al. | |
| 8,084,615 B2 | 12/2011 | Andersen et al. | |
| 2004/0229955 A1* | 11/2004 | Andersen .............. | C07C 233/83 514/616 |
| 2005/0154022 A1 | 7/2005 | Marzabadi et al. | |
| 2008/0226618 A1* | 9/2008 | Mansoor .............. | C07D 233/76 424/130.1 |
| 2009/0163496 A1 | 6/2009 | Andersen et al. | |
| 2009/0203920 A1 | 8/2009 | Welzig et al. | |
| 2010/0190766 A1 | 7/2010 | Moser et al. | |
| 2011/0212080 A1* | 9/2011 | Mansoor .............. | C07C 275/24 424/130.1 |
| 2012/0202777 A1 | 8/2012 | Brown et al. | |
| 2013/0072677 A1 | 3/2013 | Takashima et al. | |
| 2013/0231323 A1 | 9/2013 | Zhou et al. | |

FOREIGN PATENT DOCUMENTS

| | | |
|---|---|---|
| CA | 2851462 | 7/2004 |
| WO | WO9314077 | * 7/1993 |
| WO | WO1997/042179 | 11/1997 |
| WO | WO2004/062601 | 7/2004 |
| WO | WO2007/064732 | 6/2007 |
| WO | WO2007/064749 | 6/2007 |
| WO | WO2008/027466 | 3/2008 |
| WO | WO2008/154642 | 12/2008 |
| WO | WO2009/158369 | 12/2009 |
| WO | WO2010/017060 | 2/2010 |
| WO | WO2010/031750 | 3/2010 |
| WO | WO2008/105515 | 6/2010 |
| WO | WO2010/100475 | 9/2010 |
| WO | WO2011/005355 | 1/2011 |
| WO | WO2011/073845 | 3/2011 |
| WO | WO2011/045703 | 4/2011 |

(Continued)

OTHER PUBLICATIONS

Cuny "A new class of UDP-3-O-(R-3-hydroxymyristol)-N-acetylglucosamine deacetylase (LpxC) inhibitors for the treatment of gram-negative infections: PCT application WO 2008/027466," Expert Opinion on Therapeutic Patents, 2009, vol. 19, No. 6, pp. 893-899).*
Anderson, "The process of structure-based drug design," Chem Biol. 10(9):787-97 (2003).
Cas RN 1226036-58-3, entered STN May 30, 2010.
Thiel, "Structure-aided drug design's next generation," Nature Biotechnol 2:513-519 (2004).
Hale et al., "Exploring the UDP pocket of LpxC through amino acid analogs," Biorganic & Medicinal Chemistry Letters, 23(8): 2362-2367 (2013).
Lehrfeld, J., "Synthesis of 6-Substituted Nicotinic Acid Uerivatives as Analogs of Ergot Alkaloids" Journal of Medicinal Chemistry, 7(2); Jan. 1, 1964 (Jan. 1, 1964). pp. 150-154. Retrieved from the Internet: URL:http://pubs.acs.orgjjournaljjmcmar [retrieved on Nov. 30, 2011] See compounds of table III. p. 151.

(Continued)

*Primary Examiner* — Shengjun Wang
(74) *Attorney, Agent, or Firm* — McDonnell Boehnen Hulbert & Berghoff LLP

(57) ABSTRACT

Disclosed are compounds of formulae: (I) and pharmaceutically acceptable salts thereof, wherein the variables, $R_1$, $R_2$, Y, and Z are defined herein. These compounds are useful for treating Gram-negative bacteria infections.

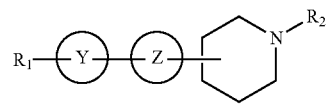

17 Claims, No Drawings

(56) References Cited

FOREIGN PATENT DOCUMENTS

| WO | WO2011/051201 | 5/2011 |
|---|---|---|
| WO | WO2011/132712 | 10/2011 |
| WO | WO2010024356 | 1/2012 |
| WO | WO2012/031298 | 3/2012 |

OTHER PUBLICATIONS

Muller et al. "Fluorine in Pharmaceuticals: Looking Beyond Intuition," Science 317, 1881-86 (2007).

Ritzen et al., "Discovery of a potent and brain penetrant mGiuR5 positive allosteric modulator," Biorganic & Medicinal Chemistry Letters, vol. 19, Apr. 24, 2009 (Apr. 24, 2009), pp. 3275-3278, See compounds on table 1, p. 3276.

Rodriguez et al., "Discovery of novel allosteric modulators of metabotropic glutamate receptor subtype 5 reveals chemical and functional diversity and invivo activity," Molecular Pharmacology, vol. 78, 2010, pp. 1105-1123, See compound on table 1, p. 1111 and tables 3-4, pp. 1117-1118.

PUBCHEM CID 14695; dated Aug. 8, 2005, pp. 1-10.
PUBCHEM CID 4339841; dated Sep. 14, 2005, pp. 1-11.
PUBCHEM CID 22013227; dated Dec. 5, 2007, pp. 1-10.
PUBCHEM CID 58670435; dated Aug. 19, 2012, pp. 1-10.
PUBCHEM CID 61211259; dated Oct. 19, 2012, pp. 1-10.
PUBCHEM CID 64990874; dated Oct. 23, 2012, pp. 1-10.
PUBCHEM CID 65712172; dated Oct. 24, 2012, pp. 1-10.
PUBCHEM CID 66573495; dated Nov. 30, 2012, pp. 1-10.
PUBCHEM CID 67642247; dated Nov. 30, 2012, pp. 1-8.
PUBCHEM CID 69475881; dated Dec. 1, 2012, pp. 1-9.
PUBCHEM CID 70691578; dated Feb. 4, 2013, pp. 1-11.

International Search Report and Written Opinion in the International Application No. PCT/US2011/050548 dated Jul. 25, 2012.

International Preliminary Report on Patentability in the International Application No. PCT/US2011/050548 dated Mar. 5, 2013.

International Search Report and Written Opinion in the International Application No. PCT/US14/51459 dated Jan. 27, 2015 (pp. 1-3).

International Preliminary Report on Patentability in the International Application No. PCT/US14/51459 dated Jan. 27, 2015 (pp. 1-8).

Written Opinion in the International Application No. PCT/US14/51459 dated Jan. 27, 2015 (pp. 1-7).

Supplementary European Search Report and European Search Opinion from the European Patent Office for Application No. 14836244.5 dated May 15, 2017 pp. 1-10.

International Search Report and Written Opinion in the International Application No. PCT/US14/51494 dated Feb. 10, 2015 (pp. 1-15).

International Preliminary Report on Patentability in the International Application No. PCT/US14/51494 dated Feb. 10, 2015 (pp. 1-6).

International Search Report and Written Opinion Issued by International Searching Authority for International Application No. PCT/US2014/51525, dated Jan. 27, 2015 (pp. 1-134).

International Preliminary Report on Patentability in the International Application No. PCT/US2014/51525, dated Jan. 27, 2015 (pp. 1-14).

International Search Report Issued by International Searching Authority for International Application No. PCT/US14/051504, dated Feb. 10, 2015 (pp. 1-3).

Written Opinion Issued by International Searching Authority for International Application No. PCT/US14/051504, dated Feb. 10, 2015 (pp. 1-6).

International Preliminary Report on Patentability in the International Application No. PCT/US14/051504, dated Feb. 10, 2015 (pp. 1-7).

Kirk, "Fluorine in medicinal chemistry: Recent therapeutic applications of fluorinated small molecules," J. Fluorine Chem. 127, 1013-29 (2006).

Purser et al., "Fluorine in medicinal chemistry," Chem. Soc. Rev. 37, 320-30 (2008).

Yale, "The Trifluoromethyl Group in Medicinal Chemistry," J. Med. Pharm. Chem. 1, 121-33 (1959).

* cited by examiner

2-PIPERIDINYL SUBSTITUTED N,3-DIHYDROXYBUTANAMIDES

CROSS-REFERENCE TO RELATED APPLICATIONS

This application is a national stage application under 35 U.S.C. § 371 of International Application No. PCT/US2014/051504, filed Aug. 18, 2014, which claims the benefit of U.S. Provisional Patent Application No. 61/866,857, filed Aug. 16, 2013, both of which are incorporated herein by reference in their entirety.

STATEMENT REGARDING FEDERALLY SPONSORED RESEARCH OR DEVELOPMENT

This invention was made with United States government support awarded by NIH Grant Nos. GM051310, AI055588, and AI094475. The United States government has certain rights in this invention.

BACKGROUND OF THE INVENTION

Field of the Invention

This invention relates to 2-piperidinyl substituted N,3-dihydroxybutanamides, and in particular, to such compounds that inhibit UDP-3-O—(R-3-hydroxydecanoyl)-N-acetylglucosamine deacetylase (LpxC), and to methods of using such compounds to treat Gram-negative bacterial infections.

Description of the Related Art

Antimicrobial resistance is increasing and becoming alarmingly common. This problem is compounded when bacterial strains are resistant to multiple antibacterials. There clearly is a need for new antibacterials, particularly antibacterials with novel mechanisms of action.

The gene lpxC encodes the enzyme uridyldiphospho-3-O—(R-hydroxydecanoyl)-N-acetylglucosamine deacetylase (LpxC). This enzyme is involved in the synthesis of lipid A, the lipid moiety of lipopolysaccharide, which is an essential component of all Gram-negative bacteria. Commercially useful LpxC inhibitors would need to both inhibit the enzymatic activity of LpxC from a variety of bacteria and defeat the resistance mechanisms of Gram-negative bacteria.

SUMMARY OF THE INVENTION

In a broad aspect, the disclosure encompasses the compounds of formula I, shown below, pharmaceutical compositions containing those compounds and methods of using such compounds to treat and/or prevent bacterial infections.

Thus, one aspect (embodiment 1) of the disclosure provides compounds of formula I:

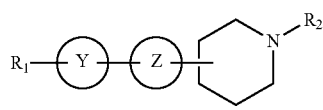

I or a pharmaceutically acceptable salt thereof, wherein
Y represents aryl optionally substituted with $R_4$, heteroaryl optionally substituted with $R_4$, or heterocyclyl optionally substituted with $R_4$;
Z represents aryl optionally substituted with $R_5$, heteroaryl optionally substituted with $R_5$, or heterocyclyl optionally substituted with $R_5$;
$R_1$ is hydrogen, aryl optionally substituted with $R_6$, heteroaryl optionally substituted with $R_6$, or heterocyclyl optionally substituted with $R_6$;
$R_2$ is

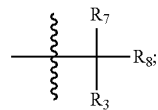

each $R_4$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy, or two $R_4$ groups when attached to the same carbon atom form =O;

each $R_5$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy, or two $R_5$ groups when attached to the same carbon atom form =O;

each $R_6$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2H$, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NHC(=NH)$NH_2$, —NH—S(O)$_{0-2}$—($C_1$-$C_6$ alkyl), —NH—S(O)$_{0-2}$-aryl, and —NH—S(O)$_{0-2}$-heteroaryl;

$R_7$ is $C_1$-$C_6$ alkyl optionally substituted with one or more $R_9$;
$R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, oxo, —$CONH_2$, —CON($C_1$-$C_6$ alkyl), —CON($C_1$-$C_6$ alkyl)$_2$, —CONH—OH, —CONH—$NH_2$, —$CO_2H$, and —$CO_2$($C_1$-$C_6$ alkyl);

$R_3$ is hydrogen or $C_1$-$C_6$ alkyl;
each $R_9$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2H$, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NHC(=NH)$NH_2$, —NH—S(O)$_{0-2}$—($C_1$-$C_6$ alkyl), —NH—S(O)$_{0-2}$-aryl, and —NH—S(O)$_{0-2}$-heteroaryl.

The disclosure also provides synthetic intermediates that are useful in making the compounds of formula I.

The disclosure also provides methods of preparing compounds of the disclosure and the intermediates used in those methods.

The disclosure also provides pharmaceutical compositions comprising a compound of formula I or a pharmaceutically acceptable salt thereof and at least one pharmaceutically acceptable carrier, solvent, adjuvant or diluent.

The disclosure also provides methods for inhibiting UDP-3-O—(R-3-hydroxydecanoyl)-N-acetylglucosamine deacetylase (LpxC), and methods of treating Gram-negative bacterial infections.

The disclosure further provides a compound or pharmaceutical composition thereof in a kit with instructions for using the compound or composition.

DETAILED DESCRIPTION OF THE INVENTION

In one embodiment, the disclosure provides compounds of formula I wherein $R_2$ is of formula:

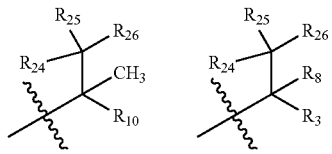

$R_{24}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —NHCONH$_2$, —NHCONH($C_1$-$C_6$ alkyl), —OCO($C_1$-$C_6$ alkyl), and —NHCO($C_1$-$C_6$ alkoxy);

$R_{25}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);

$R_{26}$ is $C_1$-$C_6$ alkyl or $C_1$-$C_6$ haloalkyl;

$R_8$ is —$CONH_2$, —CON($C_1$-$C_6$ alkyl), —CON($C_1$-$C_6$ alkyl)$_2$, —CONH—OH, —CONH—$NH_2$, —$CO_2H$, or —$CO_2$($C_1$-$C_6$ alkyl); and $R_3$ is hydrogen, $C_1$-$C_6$ alkyl. (Embodiment 2).

Particular embodiments based on formula I include those of Embodiment 3, i.e., compounds of Embodiment 2 wherein $R_{26}$ is $C_1$ haloalkyl. Other embodiments are those where $R_{26}$ is —$CH_2F$, —$CHF_2$, or —$CF_3$. (Embodiment 4) In still other embodiments based on embodiment 2, $R_{26}$ is —$CHF_2$. (Embodiment 5)

Particular embodiments based on formula I include those of Embodiment 6, i.e., compounds of Embodiment 2 wherein $R_{26}$ is $C_1$-$C_6$ alkyl. Other embodiments are those where $R_{26}$ is methyl. (Embodiment 7)

Another embodiment of the invention, i.e., Embodiment 8, encompasses compounds of any of embodiments 2-7 where $R_{25}$ is hydrogen, halogen, $C_1$-$C_6$ alkyl, or $C_1$-$C_6$ haloalkyl.

In still other embodiment based on formula I include those of Embodiment 9. i.e., compounds of Embodiment 8 wherein $R_{25}$ is hydrogen or $C_1$-$C_6$ alkyl. Other embodiments are those where $R_{25}$ is hydrogen. (Embodiment 10) In still other embodiments based on embodiment 8, $R_{25}$ is $C_1$-$C_6$ alkyl. (Embodiment 11) In Embodiment 12, which is based on formula I and embodiment 8, the compounds are those wherein $R_{25}$ is methyl.

In another embodiments based on formula I, the compounds of embodiment 2 are those wherein $R_{25}$ is methyl, and $R_{26}$ is —$CHF_2$. (Embodiment 13)

In Embodiment 14, which is based on formula I, the compounds of embodiment 2 are those wherein $R_{25}$ is hydrogen, and $R_{26}$ is —$CHF_2$.

Another embodiment of the invention, i.e., Embodiment 15, encompasses compounds of any of embodiments 2-14 where $R_{24}$ is selected from the group consisting of —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), —NHCO($C_1$-$C_6$ alkyl), —NHCONH$_2$, —NHCONH($C_1$-$C_6$ alkyl), —OCO($C_1$-$C_6$ alkyl), and —NHCO($C_1$-$C_6$ alkoxy).

In still other embodiment based on formula I include those of Embodiment 16, i.e., compounds of Embodiment 15 wherein $R_{24}$ is selected from the group consisting of —$NH_2$, —NH($C_1$-$C_6$ alkyl), —N($C_1$-$C_6$ alkyl)$_2$, —NHCO($C_1$-$C_6$ alkyl), —NHCONH$_2$, —NHCONH($C_1$-$C_6$ alkyl), and —NHCO($C_1$-$C_6$ alkoxy). Other embodiments are those where $R_{24}$ is —$NH_2$. (Embodiment 17)

In Embodiment 18, which is based on formula I and embodiment 16, the compound is where $R_{24}$ is —NHCO($C_1$-$C_6$ alkyl), —NHCONH$_2$, —NHCONH($C_1$-$C_6$ alkyl), or —NHCO($C_1$-$C_6$ alkoxy). Other embodiments are those where $R_{24}$ is —OH or $C_1$-$C_6$ alkoxy. (Embodiment 19) Yet other embodiments are those where $R_{24}$ is —OH. (Embodiment 20)

Another embodiment of the invention, i.e., Embodiment 21, encompasses compounds of any of embodiments 2-20 where $R_8$ is —CONH—OH, —CONH—$NH_2$, or —$CO_2H$.

In Embodiment 22, which is based on formula I and embodiment 21, the compound is wherein $R_8$ is —CONH—OH.

In yet other embodiments based on formula I and any one of embodiments 2-22, the disclosure provides for compounds wherein $R_3$ is hydrogen. (Embodiment 23) Other embodiments are those where $R_3$ is $C_1$-$C_6$ alkyl, or $R_3$ is methyl. (Embodiment 24)

In still other embodiments based on embodiment 2, $R_2$ is of formula:

(Embodiment 25)

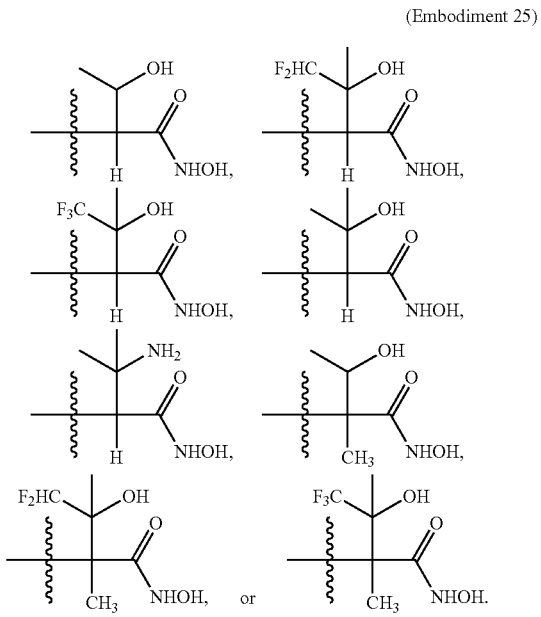

In other embodiments based on formula I, the disclosure provides for compounds wherein $R_7$ is $C_1$-$C_6$ alkyl optionally substituted with one or more $R_9$;

$R_8$ is —$CONH_2$, —$CON(C_1-C_6$ alkyl), —$CON(C_1-C_6$ alkyl)$_2$, —CONH—OH, —CONH—$NH_2$, —$CO_2H$, or —$CO_2(C_1-C_6$ alkyl); and $R_3$ is hydrogen $C_1-C_6$ alkyl. (Embodiment 26)

In Embodiment 27, which is based on formula I and embodiment 26, the compound is wherein $R_3$ is hydrogen. Embodiment 28 provides compounds wherein $R_3$ is methyl.

Another embodiment of the invention, i.e., Embodiment 29, encompasses compounds of any of embodiments 26 or 27 where $R_8$—CONH—OH or —CONH—$NH_2$. Embodiment 30 encompasses compounds of any of embodiments 26-29 where $R_7$ is $C_1-C_3$ alkyl, optionally substituted with one or more $R_9$.

Yet another embodiment of the invention, i.e., Embodiment 31, encompasses compounds of any of embodiments 26-30 where $R_9$ is independently selected from the group consisting of halogen, $C_1-C_6$ alkyl, $C_1-C_6$ haloalkyl, —$NH_2$, —$NH(C_1-C_6$ alkyl), —$N(C_1-C_6$ alkyl)$_2$, —OH, $C_1-C_6$ alkoxy, $C_1-C_6$ haloalkoxy, —SH, —$S(C_1-C_6$ alkyl), oxo, hydroxy($C_1-C_6$ alkyl), alkoxy($C_1-C_6$ alkyl), amino($C_1-C_6$ alkyl), —$CONH_2$, —$CON(C_1-C_6$ alkyl), —$CON(C_1-C_6$ alkyl)$_2$, —CONH—OH, —CONH—$NH_2$, —COH, —$CO_2H$, —$CO_2(C_1-C_6$ alkyl), —NHC(=NH)$NH_2$, —OCO($C_1-C_6$ alkyl), —NHCO($C_1-C_6$ alkoxy), —NHCO ($C_1-C_6$ alkyl), —$NHCONH_2$, and —NHCONH($C_1-C_6$ alkyl).

Particular embodiments of Formula I include those of Embodiment 32, i.e., compounds of any one of embodiments 1-31 wherein Z is phenyl optionally substituted with $R_5$.

In Embodiment 33, which is based on formula I and embodiment 32, the compound is wherein Y is phenyl optionally substituted with $R_4$. Such compounds may be of formula:

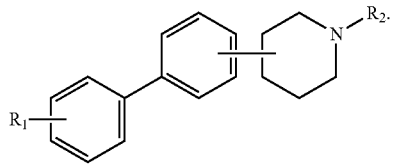

(Embodiment 34)

In Embodiment 35, which is based on formula I and embodiment 34, the compound may be represented by the formula:

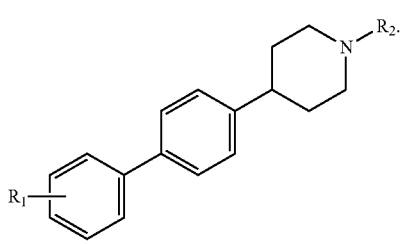

In yet other embodiments based on formula I and embodiments 32-35, the disclosure provides for compounds wherein $R_1$ is hydrogen.

Therapeutics Applications

The invention provides methods of treating Gram-negative bacterial infections, the method comprising administering to a subject in need of such treatment an effective amount of one or more compounds of the invention Particular Gram-negative bacteria are *Pseudomonas aeruginosa, Stenotrophomonas maltophilia, Burkholderia cepacia, Alcaligenes xylosoxidans, Acinetobacter, Enterobacteriaceae, Haemophilus, Neisseria species, Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis*, and *Chlamydia trachomatis*. In one embodiment, the Gram-negative bacteria is *Neisseria gonorrhoeae*. In another embodiment, the Gram-negative bacteria is *Acinetobacter Baumannii*.

Specific enterobacteriaceae is selected from the group consisting of *Serratia, Proteus, Klebsiella, Enterobacter, Citrobacter, Salmonella. Providencia. Morganella, Cedecea, Edwardsiella, Escherichia coli, Enterobacter cloacae*, and *Enterobacter aerogenes*.

In another aspect, the invention provides methods for inhibiting a deacetylase enzyme in Gram-negative bacteria, the method comprising contacting the bacteria with an effective amount of one or more compounds of the invention. A specific deacetylase enzyme is LpxC.

Pharmaceutical Compositions

In another aspect, the present disclosure provides compositions comprising one or more of compounds as described above with respect to formula I and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound (s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

Definitions

The following terms and expressions used herein have the indicated meanings.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

An "aralkyl" or "arylalkyl" group comprises an aryl group covalently attached to an alkyl group, either of which independently is optionally substituted. Preferably, the aralkyl group is aryl($C_1$-$C_6$)alkyl, including, without limitation, benzyl, phenethyl, and naphthylmethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present disclosure can modulate atherosclerosis by stimulating the removal of cholesterol from atherosclerotic lesions in a human.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"EC$_{50}$" refers to a dosage, concentration or amount of a particular test compound that elicits a dose-dependent response at 50% of maximal expression of a particular response that is induced, provoked or potentiated by the particular test compound.

"IC$_{50}$" refers to an amount, concentration or dosage of a particular test compound that achieves a 50% inhibition of a maximal response in an assay that measures such response.

Methods of Preparation

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

General Procedure

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

LC/MS analysis is conducted on an Agilent 1200 HPLC with a quadrupole mass analyzer. LC chromatography used an Agilent XDB-C18 column (4.6×50 mm, 1.8 μm) with a water/acetonitrile (each with 0.2% (v/v) formic acid) gradient at a flow rate of 0.5 mL/min. HRMS analyses are performed at the Duke MS Center. Thin-layer chromatography (TLC) is performed on Sigma-Aldrich plates with a fluorescent indicator. Proton ($^1$H) and carbon ($^{13}$C) NMR spectra are recorded at 300 and 75 MHz, respectively, on a Varian Spectrometer. Chemistry shifts (δ) are reported in parts per million (ppm) referenced to $^1$H (TMS at 0.00), $^{13}$C (DMSO at 39.55, CDCl$_3$ at 77.0, and CD$_3$OD at 49.0). Column chromatography is conducted using either silica gel (Silicycle 40-64 μm) or prepacked RediSep columns (Teledyne Isco Inc., Lincoln, Nebr.) on an Isco CombiFlash Rf instrument. All moisture-sensitive reactions are carried out using dry solvents and under a slight pressure of ultra-pure quality argon. Glassware is dried in an oven at 140° C. for at least 12 h prior to use, and then assembled quickly while hot, sealed with rubber septa, and allowed to cool under a stream of argon. Reactions are stirred magnetically using Teflon-coated magnetic stirring bars. Commercially available disposable syringes are used for transferring reagents and solvents.

The disclosures of all articles and references mentioned in this application, including patents, are incorporated herein by reference in their entirety.

EXAMPLES

The preparation of the compounds of the disclosure is illustrated further by the following scheme and examples, which are not to be construed as limiting the disclosure in scope or spirit to the specific procedures and compounds described in them. In all cases, unless otherwise specified, the column chromatography is performed using a silica gel solid phase.

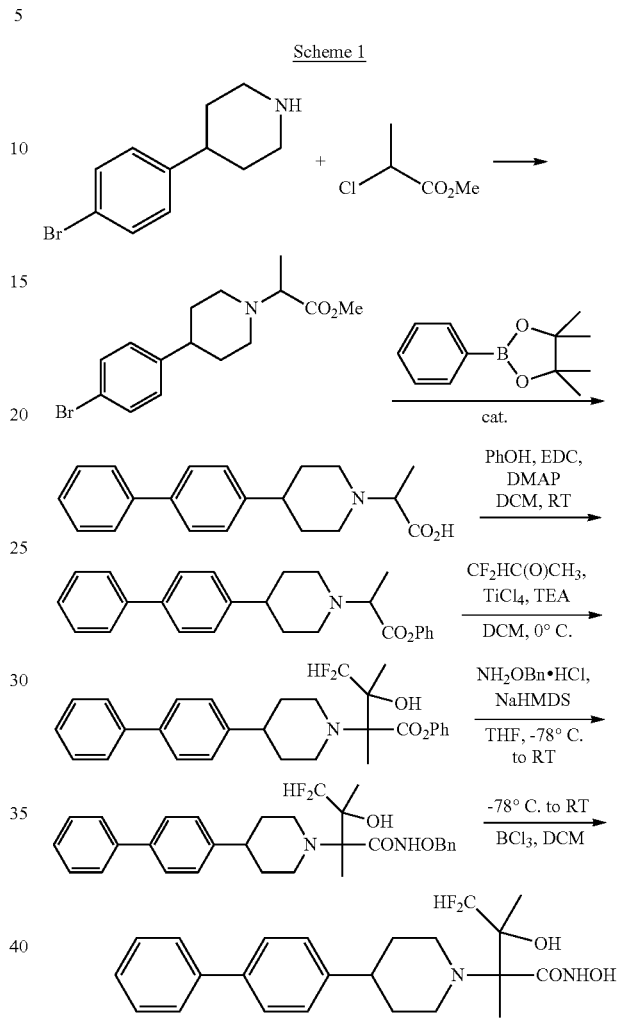

Scheme 1

Examples 1-6

The following compounds can be prepared essentially according to the procedures outlined in Scheme 1 above.

| Example No. | Compound Structure |
|---|---|
| 1 | 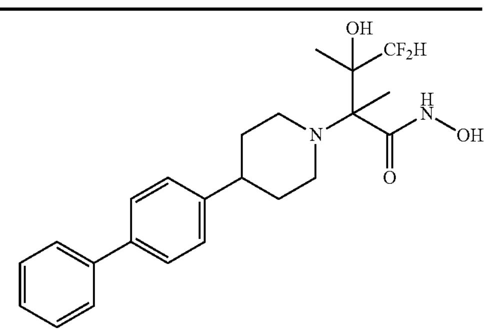 |

-continued

| Example No. | Compound Structure |
|---|---|
| 2 | 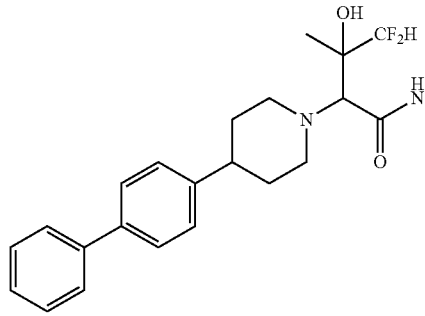 |
| 3 | 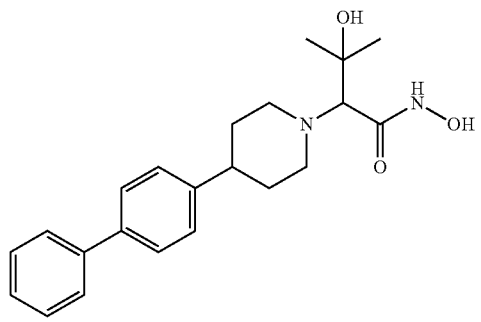 [SMILES: CC(C)(O)C(C(=O)NO)N1CCC(c2ccc(-c3ccccc3)cc2)CC1] |
| 4 | 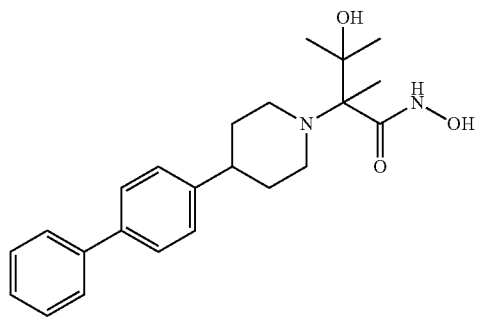 [SMILES: CC(C)(O)C(C)(C(=O)NO)N1CCC(c2ccc(-c3ccccc3)cc2)CC1] |
| 5 | 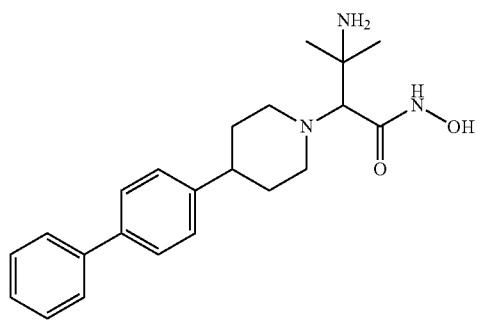 |

-continued

| Example No. | Compound Structure |
|---|---|
| 6 | 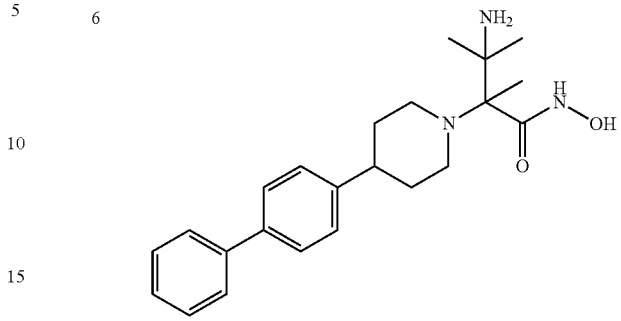 |

Example 7

Biological Examples

Protein Purification

Plasmids encoding wild-type *E. coli* LpxC, *P. aeruginosa* LpxC (residues 1-299) with a C40S mutation, and *A. aeolicus* LpxC lacking the eight C-terminal amino acids and containing a C181A mutation (1-274) are prepared following established procedures. An *E. coli* LpxC construct lacking the C-terminal five amino acids (1-300) is prepared by using the QuikChange site-directed mutagenesis kit (Stratagene) from the full-length *E. coli* LpxC gene. LpxC proteins are overexpressed in BL21(DE3)STAR cells (Invitrogen) grown in LB media and purified using anion-exchange (Q-Sepharose Fast Flow, Amersham) and size exclusion (Sephacryl S-200 HR, Amersham) chromatography. Purified proteins are concentrated and buffer-exchanged into 25 mM HEPES, pH 7.0, with 100 mM KCl and 0.1 mM $ZnSO_4$. For the EcLpxC proteins, 2 mM dithiothreitol is added to all the purification buffers. All proteins samples for enzymatic assay and crystallography are stored at −80° C.

Enzymatic Inhibition Assay

UDP-3-O—[(R)-3-hydroxymyristoyl]-N-acetylglucosamine and [α-$^{32}$P]UDP-3-O—[(R)-3-hydroxymyristoyl]-N-acetylglucosamine are prepared as previously described. Assays of LpxC activity are performed at 30° C. in 25 mM sodium phosphate, pH 7.4, 1 mg/mL bovine serum albumin, 100 mM KCl and 2 mM DTT, in the presence of 5 μM substrate and 0.2 nM EcLpxC, unless noted otherwise. 10% DMSO is included and held constant in assay mixtures. Initial velocities are calculated from the linear portion of reaction progress curves (<10% conversion of substrate to product).

$K_M$ and $V_{max}$ values are determined by varying the substrate concentration from 0.5 to 50 μM. Data is analyzed using an Eadie-Hofstee plot and by a nonlinear curve-fitting program (KaleidaGraph, Synergy Software); the resultant values are nearly identical within experimental errors. To determine a $K_I$ value, the compound concentrations are varied from 12.5 pM to 15 nM, or from 0.8 pM to 51 nM. Fractional activity ($u_i/u_0$) versus the compound concentration is plotted and fitted to calculate a $K_I^{app}$ value using the Morrison equation:

$$\frac{v_i}{v_0} = 1 - \frac{([E]_T + [I]_T + K_I^{app}) - \sqrt{([E]_T + [I]_T + K_I^{app})^2 - 4[E]_T[I]_T}}{2[E]_T}$$

where $u_i$ is the initial velocity of the reaction in the presence of the inhibitor, $u_0$ is the initial velocity of the reaction in the absence of the inhibitor, $[E]_T$ is the total enzyme concentration, and $[I]_T$ is the total inhibitor concentration. A $K_I$ value is calculated using: $K_I = K_I^{app}/(1+[S]/K_M)$, where [S] is the substrate concentration. All measurements are done in triplicates.

Construction of E. coli W3110PA

P. aeruginosa lpxC is used to replace E. coli chromosomal lpxC. A linear PCR product containing the P. aeruginosa ORF with flanking sequences containing 33 bps of DNA complementary to the upstream 5' region of E. coli lpxC and 45 bps of DNA complementary to the downstream 3' region of E. coli lpxC, is amplified from a plasmid carrying P. aeruginosa lpxC using primers pa-LpxC-5' (5'-TCG GTT GGA TAG GTA ATT TGG CGA GAT AAT ACG ATG ATC AAA CAA CGC ACC TTG AAG AAC ATC-3') and pa-LpxC-3' (5'-GTG CCA GAT TTG CCA GTC GAA TTT TAT ACG ACA GTA TAA ATG TCG CTA CAC TGC CGC CGC C-3'). This PCR product is gel purified and then electroporated into E. coli DY330 cells, which carry λ-red recombinases, using a Bio-Rad Gene Pulser II set to 2.5 kV, 25 μF, and 400Ω. While DY330 cannot survive on the LB/agar plate supplemented with 15 μg/mL of the compound of disclosure, cells wherein E. coli lpxC replaced with P. aeruginosa lpxC can survive on this media. Transformants are therefore selected directly using the compound of disclosure without introducing a closely linked resistance cassette for a different antibiotic marker. Genomic DNA from resistant colonies is isolated, and the region around lpxC amplified with primers 300-up-lpxC (5'-ACA AAC GTC CTG AAA TCA CTC TGG TG-3') and 300-down-lpxC (5'-TCC CTA ATA AGA GAT GCG GCC AGA A-3'), and sequenced with primers paLpxC-361-5' (5'-GAG CAG GAA GCT GCC AA-3') and paLpxC-581-3' (5'-GTA CTC GAT GTC GCG CA-3'). One clone in which PalpxC had replaced chromosomal EclpxC is selected and grown at 30° C. This strain is used to generate P1vir lysate, which is used transduce chromosomal PalpxC into the chromosome of E. coli W3110. Transduced cells are plated on LB/agar containing 15 μg/mL of the compound of disclosure and 10 mM sodium citrate. The resulting colonies are purified 3 times on this media. Genomic DNA from resistant colonies is isolated, and the region around lpxC is amplified with the primers 300-up-lpxC and 300-down-lpxC, and sequenced with paLpxC-361-5' and paLpxC-581-3'. The colony that harbored the P. aeruginosa lpxC knock-in is named as W3110PA.

Minimum Inhibitory Concentration (MIC)

MICs are determined according to the NCCLS protocol using 96-well plates. Briefly, diluted bacterial cells ($10^6$ cells/mL) are added into each well of the 96-well plates containing LB medium with 5% DMSO and various concentrations of the compound of disclosure. After incubation of the plates for 22 hours at 37° C., [4,5-dimethylthiazol-2-yl]-2,5-diphenyltetrazolium bromide solution (MTT) is added (final concentration, 0.2 mg/mL) and incubated at 37° C. for another 3 hrs. MIC is determined as the lowest concentration of an antibiotic that prevented color change (yellow to purple).

The antibiotic activities of several exemplary compounds useful in the methods of the disclosure are evaluated by measurements of minimum inhibitory concentrations (MICs) using wild-type E. coli (W3110), P. aeruginosa (PAO1), and modified E. coli strains with the native lpxC gene replaced by that of R. leguminosarum (W3110RL) or P. aeruginosa (W3110PA).

Compounds of the invention have MIC values generally ranging from about 0.01 μg/ml to about 400 μg/ml.

The antibiotic activities of several exemplary compounds useful in the methods of the disclosure are evaluated by measurements of minimum inhibitory concentrations (MICs) using two N. gonorrhoeae strains: FA19 (a drug-sensitive strain) and 35/02 (drug-resistant strain.) FA19 is an isolate from uncomplicated infection and was lyophilized in 1962. 35/02 displays intermediate-level resistance to extended spectrum cephalosporins such as ceftriaxone (MIC=0.12 μg/ml) and cefixime (MIC=0.28 μg/ml) and high-level resistance to penicillin (MIC=6 μg/ml). The strain is being sequenced to elucidate the mechanisms involved in high-level chromosomally mediated resistance.

Disk Diffusion Assay

An assay was performed on two strains of Acinetobacter Baumannii: antibiotic susceptible strain (Sus. A.b. Isolate), and multidrug-resistant strains (MDR A.b. Isolate). 2 μg of compound is added per disc, which is 6 mm in diameter. Activity is measured as the diameter (in mm) of the growth inhibition.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A compound that is:

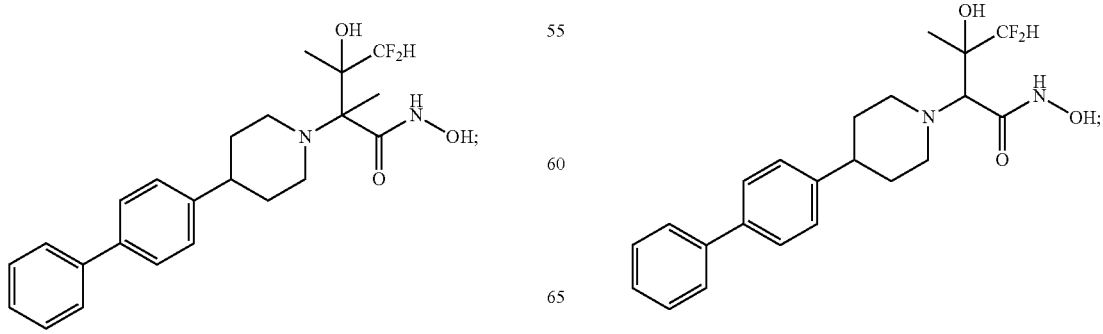

-continued

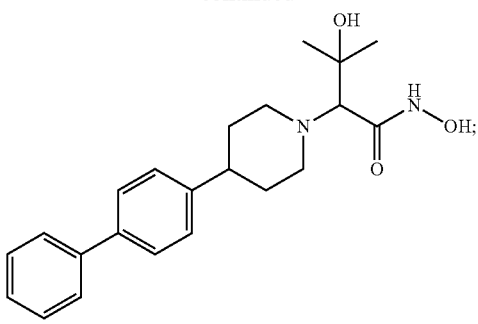 [SMILES: CC(C)(N)C(C)(C(=O)NO)N1CCC(c2ccc(-c3ccccc3)cc2)CC1]

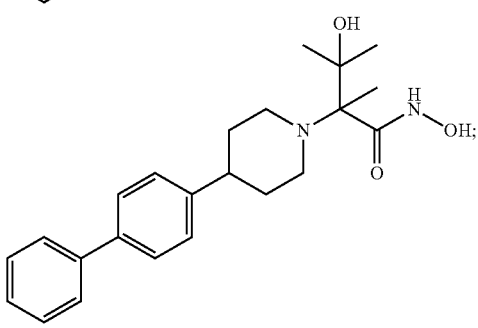

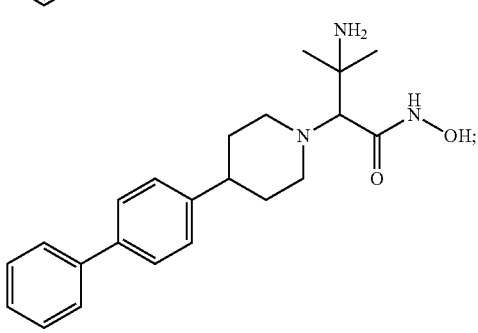

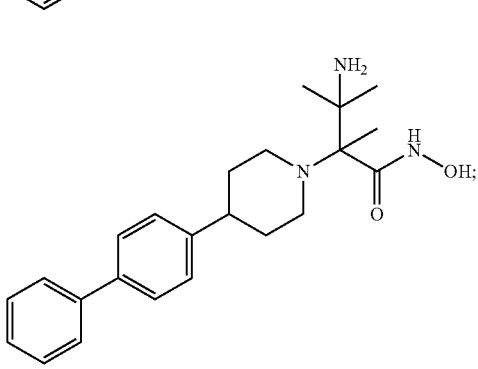

or pharmaceutically acceptable salts thereof.

2. A pharmaceutical composition comprising a compound according to claim 1 and a pharmaceutically acceptable carrier, solvent, adjuvant or diluent.

3. A method of treating Gram-negative bacterial infections, the method comprising administering to a subject in need of such treatment an effective amount of one or more compounds according to claim 1.

4. A method of inhibiting a deacetylase enzyme in Gram-negative bacteria, the method comprising administering to a subject in need of such treatment an effective amount of one or more compounds according to claim 1.

5. A compound of formula:

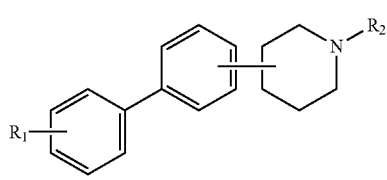

or a pharmaceutically acceptable salt thereof, wherein $R_1$ is hydrogen; and $R_2$ is

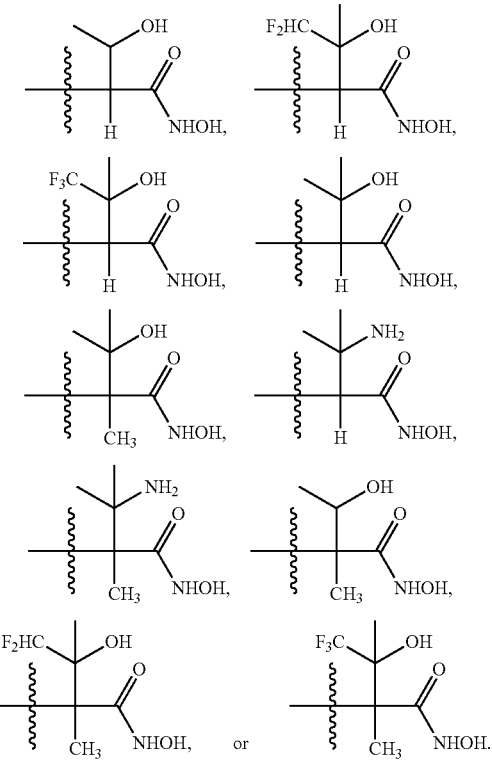

6. A compound according to claim 5, wherein the compound is of formula:

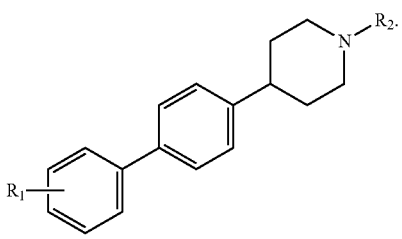

7. A compound according to claim 5, wherein $R_2$ represents

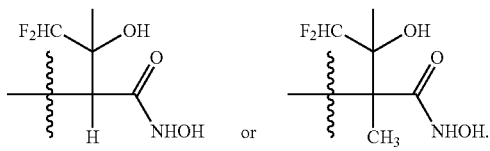

8. A compound according to claim 5, wherein R₂ represents

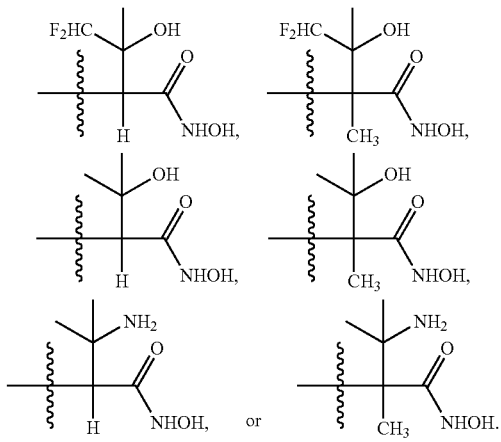

9. A compound according to claim 5 that is:

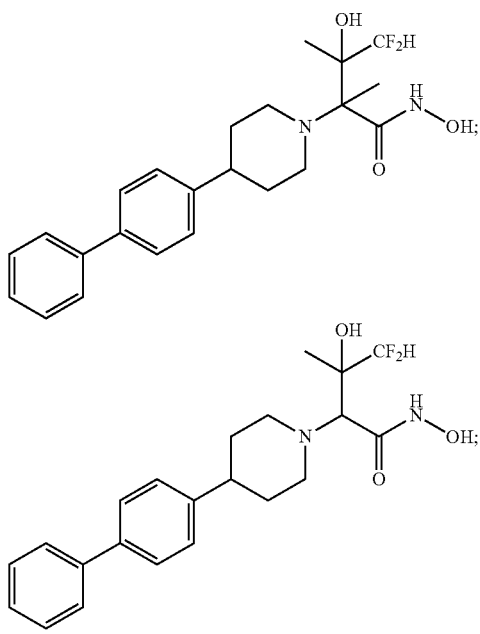

or pharmaceutically acceptable salts thereof.

10. A pharmaceutical composition comprising a compound according to claim 5 and a pharmaceutically acceptable carrier, solvent, adjuvant or diluent.

11. A method of treating Gram-negative bacterial infections, the method comprising administering to a subject in need of such treatment an effective amount of one or more compounds according to claim 5.

12. A method of inhibiting a deacetylase enzyme in Gram-negative bacteria, the method comprising administering to a subject in need of such treatment an effective amount of one or more compounds according to claim 5.

13. A compound of the formula:

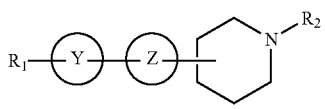

or a pharmaceutically acceptable salt thereof, wherein
Y represents phenyl optionally substituted with R₄;
Z represents phenyl optionally substituted with R₅;
R₁ is hydrogen;
R₂ is

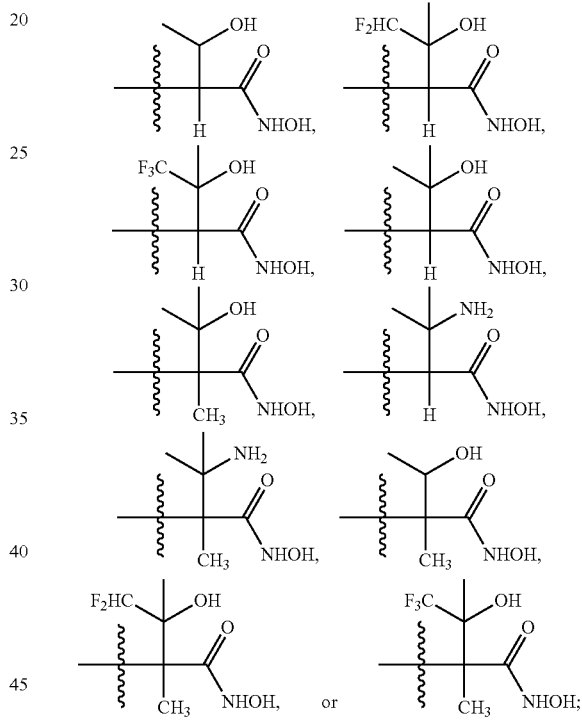

each R₄ is independently selected from the group consisting of halogen, —NO₂, —CN, C₁-C₆ alkyl, C₁-C₆ haloalkyl, —NH₂, —NH(C₁-C₆ alkyl), —N(C₁-C₆ alkyl)₂, —OH, C₁-C₆ alkoxy, and C₁-C₆ haloalkoxy; and each R₅ is independently selected from the group consisting of halogen, —NO₂, —CN, C₁-C₆ alkyl, C₁-C₆ haloalkyl, —NH₂, —NH(C₁-C₆ alkyl), —N(C₁-C₆ alkyl)₂, —OH, C₁-C₆ alkoxy, and C₁-C₆ haloalkoxy.

14. A compound according to claim 13, wherein R₂ represents

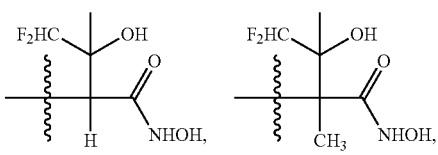

-continued

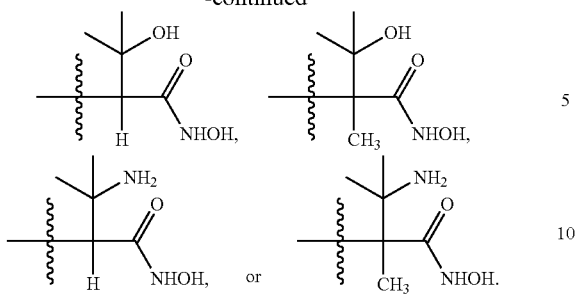

15. A pharmaceutical composition comprising a compound according to claim 13 and a pharmaceutically acceptable carrier, solvent, adjuvant or diluent.

16. A method of treating Gram-negative bacterial infections, the method comprising administering to a subject in need of such treatment an effective amount of one or more compounds according to claim 13.

17. A method of inhibiting a deacetylase enzyme in Gram-negative bacteria, the method comprising administering to a subject in need of such treatment an effective amount of one or more compounds according to claim 13.

* * * * *

SEQUENCE LISTING

```
<160> NUMBER OF SEQ ID NOS: 6

<210> SEQ ID NO 1
<211> LENGTH: 63
<212> TYPE: DNA
<213> ORGANISM: Artificial Sequence
<220> FEATURE:
<223> OTHER INFORMATION: Synthetic; pa-LpxC-5' Primer

<400> SEQUENCE: 1
tcggttggat aggtaatttg gcgagataat acgatgatca aacaacgcac cttgaagaac    60
atc                                                                  63

<210> SEQ ID NO 2
```

```
<211> LENGTH: 61
<212> TYPE: DNA
<213> ORGANISM: Artificial Sequence
<220> FEATURE:
<223> OTHER INFORMATION: Synthetic; pa-LpxC-3' Primer

<400> SEQUENCE: 2
gtgccagatt tgccagtcga attttatacg acagtataaa tgtcgctaca ctgccgccgc    60
c                                                                   61

<210> SEQ ID NO 3
<211> LENGTH: 26
<212> TYPE: DNA
<213> ORGANISM: Artificial Sequence
<220> FEATURE:
<223> OTHER INFORMATION: Synthetic; 300-up-lpxC Primer

<400> SEQUENCE: 3
acaaacgtcc tgaaatcact ctggtg                                        26

<210> SEQ ID NO 4
<211> LENGTH: 25
<212> TYPE: DNA
<213> ORGANISM: Artificial Sequence
<220> FEATURE:
<223> OTHER INFORMATION: Synthetic; 300-down-lpxC Primer

<400> SEQUENCE: 4
tccctaataa gagatgcggc cagaa                                         25

<210> SEQ ID NO 5
<211> LENGTH: 17
<212> TYPE: DNA
<213> ORGANISM: Artificial Sequence
<220> FEATURE:
<223> OTHER INFORMATION: Synthetic; paLpxC-361-5' Primer

<400> SEQUENCE: 5
gagcaggaag ctgccaa                                                  17

<210> SEQ ID NO 6
<211> LENGTH: 17
<212> TYPE: DNA
<213> ORGANISM: Artificial Sequence
<220> FEATURE:
<223> OTHER INFORMATION: Synthetic; paLpxC-581-3' Primer

<400> SEQUENCE: 6
gtactcgatg tcgcgca                                                  17
```